US008591413B2

(12) United States Patent
Kruglick

(10) Patent No.: US 8,591,413 B2
(45) Date of Patent: Nov. 26, 2013

(54) ECHOGRAM DETECTION OF SKIN CONDITIONS

(75) Inventor: Ezekiel Kruglick, Poway, CA (US)

(73) Assignee: Empire Technology Development LLC, Wilmington, DE (US)

( * ) Notice: Subject to any disclaimer, the term of this patent is extended or adjusted under 35 U.S.C. 154(b) by 934 days.

(21) Appl. No.: 12/714,060

(22) Filed: Feb. 26, 2010

(65) Prior Publication Data

US 2011/0213223 A1 Sep. 1, 2011

(51) Int. Cl.
*A61B 19/00* (2006.01)

(52) U.S. Cl.
USPC .......................................... 600/306; 128/916

(58) Field of Classification Search
USPC .......................................... 600/306; 128/916
See application file for complete search history.

(56) References Cited

U.S. PATENT DOCUMENTS

| | | | | |
|---|---|---|---|---|
| 4,031,743 | A * | 6/1977 | Kossoff et al. | 73/629 |
| 2004/0015082 | A1 * | 1/2004 | Vernet | 600/450 |
| 2005/0228280 | A1 * | 10/2005 | Ustuner et al. | 600/443 |
| 2006/0227137 | A1 | 10/2006 | Weyrich et al. | |
| 2006/0239547 | A1 | 10/2006 | Robinson | |
| 2006/0239574 | A1 | 10/2006 | Brower et al. | |
| 2007/0020623 | A1 | 1/2007 | Petersohn | |
| 2007/0049832 | A1 | 3/2007 | Edgar | |
| 2007/0232962 | A1 * | 10/2007 | Zumeris et al. | 601/2 |
| 2008/0139900 | A1 * | 6/2008 | Randlov et al. | 600/306 |
| 2008/0200777 | A1 * | 8/2008 | Issachar et al. | 600/306 |
| 2009/0174878 | A1 | 7/2009 | Wadman | |

FOREIGN PATENT DOCUMENTS

| | | | |
|---|---|---|---|
| EP | 1795131 A1 | * | 8/2007 |
| SU | 1833817 | * | 10/1990 |
| WO | 2009115947 A1 | | 9/2009 |
| WO | 2009145735 A1 | | 12/2009 |

OTHER PUBLICATIONS

Weyrich, Analysis of Human Faces using a Measurement-Based Skin Reflectance Model; Article; 2006; 12 pages.
D'Eon, Advanced Techniques for Realistic Real-Time Skin Rendering; Chapter 14 from book GPU Gems 3; 58 pages.
Pellacani, In vivo asseessment of melanocytic nests in nevi and melanomas by reflectance confocal microscopy; Article, Modern Pathology (2005) 18; 6 pages.
Igarashi, The Appearance of Human Skin; Technical Report CUCS-024-05; Jun. 2005; 88 pages; New York NY, USA.
Thalmann, Virtual Clothes, Hair and Skin for Beautiful Top Models; Article; 1998; 19 pages.
Jensen, A Practical Model for Subsurface Light Transport; Article Aug. 2001; 8 pages; Los Angeles CA, USA.
Tsumura, Image-based skin color and texture analysis/synthesis by extracting hemoglobin and melanin information in the skin; Article; 10 pages.

(Continued)

*Primary Examiner* — Patricia Mallari
*Assistant Examiner* — Puya Agahi
(74) *Attorney, Agent, or Firm* — Jensen & Puntigam, PS

(57) ABSTRACT

Technologies adapted for using acoustic pulses to diagnose skin conditions are disclosed. A series of acoustic pulses may be directed at a skin through the speaker of a device. Acoustic reflections may be received at a microphone. The reflections may be sampled and stored as echogram data. The echogram may be analyzed to identify potential skin conditions.

25 Claims, 7 Drawing Sheets

(56) References Cited

OTHER PUBLICATIONS

Yovel, Plant Classification from Bat-Like Echolocation Signals; Article; 2008; vol. 4, Issue 3, PLOS Computational Biology; 13 pages.

U.S. Appl. No. 12/714,011; Multidirectional Scan and Algorithmic Skin Health Analysis; filed Feb. 26, 2010.

Agero, A.L.C., et al., "Reflectance confocal microscopy of pigmented basal cell carcinoma," Journal of the American Academy of Dermatology, 2006, vol. 54, No. 4, pp. 638-643.

Barnard, C.M, and Goldyne, M.E., "Evaluation of an Asynchronous Teleconsultation System for Diagnosis of Skin Cancer and Other Skin Diseases," Telemedicine Journal and e-Health, Jul. 9, 2004, vol. 6 No. 4, pp. 379-384.

Cassileth, B.R., et al., "How well do physicians recognize melanoma and other problem lesions?," Journal of the American Academy of Dermatology, Apr. 1986, vol. 14, Vo.4, pp. 555-560.

Claridge, E. and Preece, S. J., "An inverse method for the recovery of tissue parameters from colour images," Information Processing in Medical Imaging, Jul. 20-25, 2003, pp. 306-317.

Cotton, S.D., and Claridge, E., "Developing a predictive model of human skin colouring," Proceedings of SPIE Medical Imaging, 1996, vol. 2708, pp. 814-825.

Curiel-Lewandrowski, C., et al., "Use of In Vivo Confocal Microscopy in Malignant Melanoma," An Aid in Diagnosis and Assessment of Surgical and Nonsurgical Therapeutic Approaches, Archives of Dermatology, vol. 140, No. 9, pp. 1127-1132.

Donner, C. and Jensen, H. W., "Light Diffusion in Multi-Layered Translucent Materials," Proceedings of ACM SIGGRAPH, Jul. 31-Aug. 4, 2005, vol. 24, No. 3, pp. 1032-1039.

Donner, C., et al., "A Layered, Heterogeneous Reflectance Model for Acquiring and Rendering Human Skin," ACM Transactions on Graphics, Dec. 2008, vol. 27, No. 5, pp. 1-12.

Gerbert, B., et al., "Primary Care Physicians as Gatekeepers in Managed Care," Archives of Dermatology, Sep. 1996, vol. 132, No. 9, pp. 1030-1038.

Gonzalez, S. and Gilaberte-Calzada, Y., "In vivo reflectance-mode confocal microscopy in clinical dermatology and cosmetology," International Journal of Cosmetic Science, 2008, vol. 30, No. 1, pp. 1-17.

Howard, K.K., et al., "Evaluation of Melanoma/Skin Cancer Screening in Massachusetts," Preliminary Results, Cancer, Jan. 15, 1990, vol. 65 No. 2, pp. 375-379.

Jerant, A.F, et al., "Early Detection and Treatment of Skin Cancer," American Family Physician, Jul. 15, 2000, vol. 62, No. 2, pp. 357-368.

Marghoob, A.A., et al., "Instruments and newtechnologies for the in vivodiagnosis of melanoma," Journal of the American Academy of Dermatology, Nov. 2003, vol. 49, No. 5, pp. 777-797.

Miles, F., and Meehan, J.W., "Visual discrimination of pigmented skin lesions," Health Psychology, Mar. 1995, vol. 14, No. 2, pp. 171-177.

Miller, K.E., "Early Detection of Metastatic Melanoma Using Ultrasound," American Family Physician, Dec. 1, 2000, vol. 62, No. 11, pp. 2522.

Nickell, S., et al., "Anisotropy of light propagation in human skin," Physics in Medicine and Biology, 2005, vol. 45, No. 10, pp. 2873-2886.

Oksala, A., "Echogram in Melanoma of the Choroid*," British Journal of Ophthalmology, Jul. 1959. vol. 43, No. 7, pp. 408-414.

Ramsay, D.L, and Fox, A.B., "The Ability of Primary Care Physicians to Recognize the Common Dermatoses," Archives of Dermatology, Oct. 1981, vol. 117, No. 10, pp. 620-622.

Lucid, Inc., "New Studies Show Effectiveness of Reflective Confocal Microscopy," Press Release, accessed at http://www.prlog.org/10026545-new-studies-show-effectiveness-of-reflective-confocal-microscopy.html, accessed on Aug. 7, 2007, pp. 2.

Wagner, R.F., et al., "Residents'Corner: Diagnoses of Skin Disease: Dermatologists vs. Nondermatologists (abstract)," The Journal of Dermatologic Surgery and Oncology, 1985, vol. 11, No. 5, pp. 476-479.

Wolbarsht, M.L., "A proposal to localize an intraocular melanoma by photoacoustic spectroscopy," Soviet Journal of Quantum Electronics, 1981, vol. 11, No. 12, pp. 1623-1624.

International Search Report and Written Opinion for International Application No. PCT/US2010/046694, mailed on Jul. 5, 2011.

Remaly, Office Action in U.S. Appl. No. 12/714,011, Nov. 8, 2012, 19 pages.

Remaly, Office Action in U.S. Appl. No. 12/714,011, Mar. 28, 2013, 11 pages.

Remaly, Office Action in U.S. Appl. No. 12/714,011, May 22, 2013, 11 pages.

* cited by examiner

ECHOGRAM DETECTION OF SKIN CONDITIONS

CROSS-REFERENCE TO RELATED APPLICATIONS

This application is related by subject matter to U.S. patent application Ser. No. 12/714,011, filed Feb. 26, 2010, entitled "MULTIDIRECTIONAL SCAN AND ALGORITHMIC SKIN HEALTH ANALYSIS", which is hereby incorporated by reference.

BACKGROUND

Unless otherwise indicated herein, the materials described in this section are not prior art to the claims in this application and are not admitted to be prior art by inclusion in this section.

Large scale tests performed in 1986 and 1987 demonstrated that it may be feasible to conduct effective large scale visual screening for melanoma and other malignant skin lesions. Howard K. Koh et al., "Evaluation of melanoma/skin cancer screening in Massachusetts: Preliminary results," *Cancer* 65, no. 2 (1990), pages 375-379. Such screening could dramatically reduce costs of care and improve life.

Unfortunately, the cost of routine screening by dermatologists is prohibitive. To this day the majority (about 90%) of health systems pay only for screening by a "gatekeeper", generally a patient's primary care physician. C. M. Barnard and M. E. Goldyne, "Evaluation of an asynchronous teleconsultation system for diagnosis of skin cancer and other skin diseases," *Telemedicine Journal and e-Health* 6, no. 4 (2000), pages 379-384. Non-specialists such as most primary care physicians have only a 50% probability of identifying malignant skin lesions—functionally equivalent to flipping a coin. See, e.g., Ramsay D L, Fox A B, "The ability of primary care physicians to recognize the common dermatoses," *Arch Dermatol* 117, (1981), pages 620-622; and Cassileth B. R., Clark W. H. Jr., Lusk E. J., et al., "How well do physicians recognize melanoma and other problem lesions?" *J. Am. Acad. Dermatol.* 14 (1986), pages 555-560.

The present disclosure identifies and appreciates that conventional approaches of screening for certain skin conditions are limited and inadequate, due to prohibitive costs of doing so effectively, and that improved accuracy screening technologies allowing automated screening and/or screening by non-specialist medical caregivers, for skin features that involve more than cosmetic skin alteration, would be beneficial for better advance detection of skin conditions.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
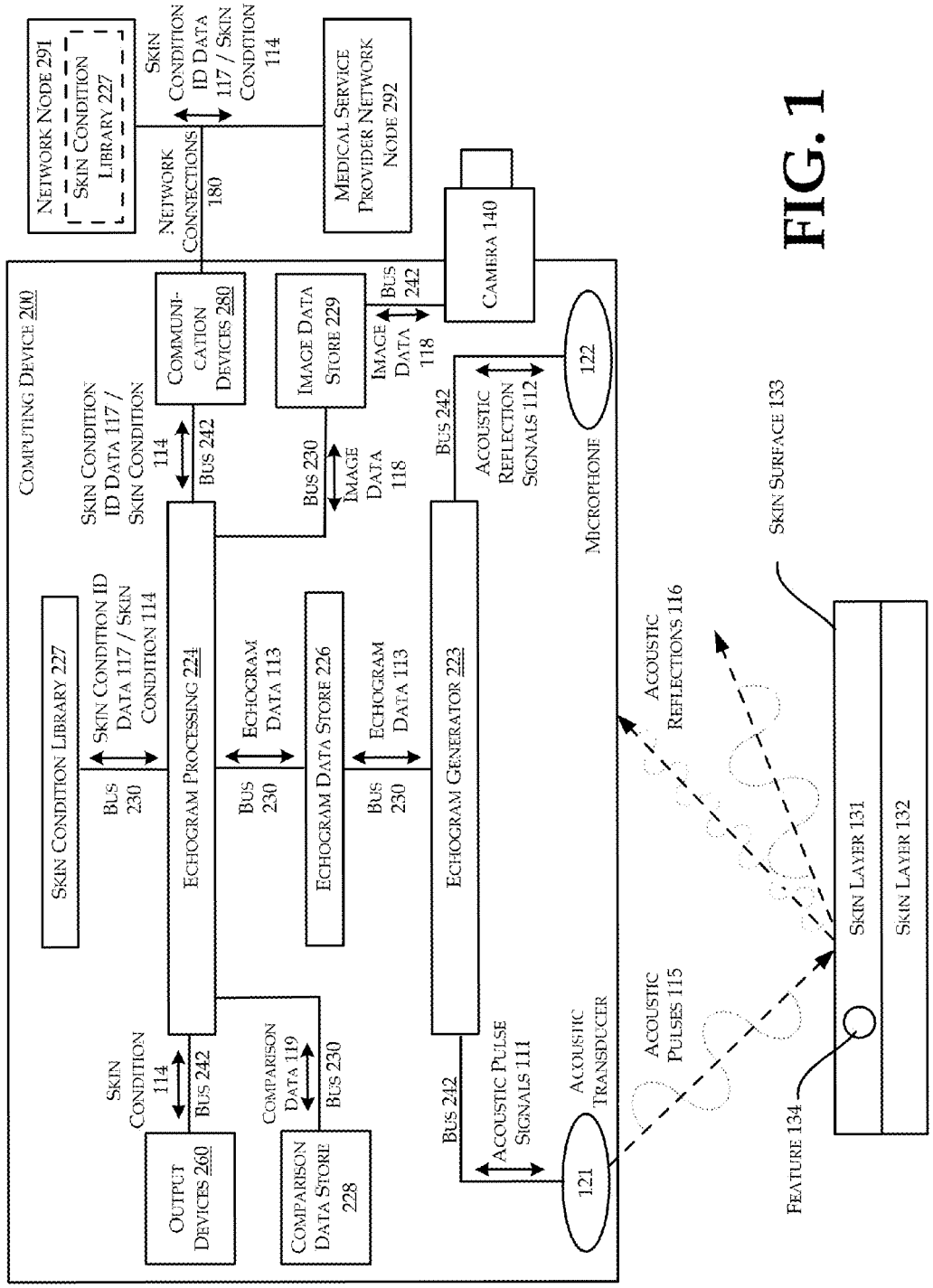
FIG. 1 is a diagram illustrating an example device configured to generate echogram data and analyze the echogram data to determine potential skin conditions.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and made part of this disclosure.

The present disclosure is generally drawn, inter alia, to methods, devices, and/or systems related to using acoustic pulses to diagnose skin conditions. A series of acoustic pulses may be directed at a skin through the speaker of a device. Acoustic reflections may be received at a microphone. The reflections may be sampled and stored as echogram data. The echogram may be analyzed to identify potential skin conditions.

FIG. 1 is a diagram illustrating an example device configured to generate echogram data and analyze the echogram data to determine potential skin conditions, arranged in accordance with at least some embodiments of the present disclosure. FIG. 1 comprises a computing device 200, network nodes 291 and 292, and a skin comprising a skin surface 133, a skin layer 131, a skin layer 132, and a feature 134. Computing device 200 may comprise one or more of an echogram generator 223, an acoustic transducer 121, a microphone 122, and an echogram data store 226. Computing device 200 may further comprise one or more of echogram processing 224, skin condition library 227, output devices 260, comparison data store 228, camera 140, image data store 229, and/or communication devices 280. Network node 291 may also comprise a skin condition library 227.

In FIG. 1, the echogram generator 223 may be coupled to the acoustic transducer 121 via bus 242 over which acoustic pulse signals 111 may be transmitted. Acoustic transducer 121 may be adapted to produce acoustic pulses 115 that are directed at the skin. Acoustic pulses 115 may reflect off the skin as acoustic reflections 116. Acoustic reflections 116 may comprise reflections of similar wavelengths as the pulses 115, as well as subwavelength acoustic reflections corresponding to reflecting features, such as feature 134, which comprise at least one dimension smaller than a corresponding acoustic pulse wavelength from the series of acoustic pulses 115. Acoustic reflections 116 may be received at microphone 122.

Microphone 122 may be coupled to the echogram generator 223 via bus 242, over which acoustic reflection signals 112 may be transmitted. Echogram generator 223 may be configured to store echogram data 113 in echogram data store 226 via bus 230.

In FIG. 1, the echogram processing 224 may be configured to read echogram data 113 in the echogram data store 226 via bus 230. Echogram processing 224 may be adapted to extract characteristics of the echogram data 113 for use in identifying a skin condition 114. Echogram processing 224 may also be arranged to extract characteristics of image data 118 from image data store 229 via bus 230. Camera 140 may be adapted to store image data 118 in image data store 229 via bus 242. Echogram processing 224 may also be configured to extract characteristics of comparison data 119 in comparison data store 228 via bus 230. Echogram processing 224 may be arranged to aggregate the extracted echogram characteristics, image characteristics, and/or comparison characteristics as skin condition ID data 117, and echogram processing 224 may be adapted to use the skin condition ID data 117 to look up a skin condition 114 in the skin condition library 227 via bus 230. Echogram processing 224 may also be adapted to look up skin condition 114 by communicating skin condition ID data 117 with communications devices 280 via bus 242, causing the communication devices 280 to communicate skin condition ID data 117 with network nodes 291 and 292, via network connections 180. Echogram processing 224 may also be arranged to output skin condition 114 to output devices 260 via bus 242.

Computing device 200 may be configured to generate echogram data 113 corresponding to the skin, using the echogram generator 223, in conjunction with the acoustic transducer 121 and microphone 122. Computing device 200 may be further configured to use echogram processing 224 to identify a skin condition 114 based on the echogram data 113 as well as any other available data. Echogram processing 224 may also be arranged to use a variety of resources including one or more of the skin condition library 227, the comparison data store 228, the network nodes 291 and 292, and/or the image data store 229, to identify one or more skin conditions 114.

Computing device 200 may be configured in any of a wide range of configurations. In some embodiments, computing device 200 may comprise a mobile device, such as a device comprising a mobile telephone. The acoustic transducer 121 may comprise a speaker used for voice communications of the mobile telephone. The microphone 122 may comprise a microphone used for voice communications of the mobile telephone. The camera 140 may comprise a digital camera integrated into the mobile device. The network connections 180 may comprise wireless connections, such as cellular communications connections. An application configured to execute on mobile device hardware may comprise echogram generator 223 and echogram processing 224, and may use mobile device hardware to create and/or access one or more of a comparison data store 228, an image data store 229, output devices 260, communication devices 280, an acoustic transducer 121, and/or a microphone 122. An example computing device 200 is illustrated in further detail in FIG. 2.

In some embodiments, some aspects of the computing device 200 may be provided by one or more special purpose attachments. Special purpose attachments may be couplable with the computing device 200 and detachable from the computing device 200 such that the computing device 200 remains operable for functions not including the attachments. For example, in order to produce high quality acoustic pulses over a wide range of frequencies, an attachment comprising a special purpose transducer 121, a microphone 122 and/or an echogram generator 223 may be coupled to the computing device 200.

In some embodiments, computing device 200 may be configured with an echogram User Interface (UI) allowing a user of the device 200 to procure an echogram comprising echogram data 113, optionally take a picture of skin corresponding to the echogram to procure image data 118, and/or correlate the image data 118 with the echogram data 113, along with any comparison data 119 from previous echograms and/or images of the skin. The correlated data may then be sent as skin condition ID data to one or more of the network nodes 291 and 292 for diagnosis, or may be diagnosed at the device 200 using a skin condition library 227 located on the device 200.

Echogram generator 223 and acoustic transducer 121 may be configured to produce a series of acoustic pulses 115. The echogram generator 223 may produce acoustic pulse signals 111 which are converted to acoustic pulses 115 by the acoustic transducer 121. The series of acoustic pulses may for example comprise two or more acoustic pulses. Each acoustic pulse in the series may comprise one or more frequencies. The one or more frequencies of an acoustic pulse may be different from frequencies of one or more other acoustic pulses in the series. By employing a series of acoustic pulses 115 comprising a variety of frequencies, the echogram generator 223 may be able to obtain more data about the skin that would otherwise be achievable using pulses of only one frequency. An example echogram generator 223 is illustrated in further detail in FIG. 3 and FIG. 4.

Echogram generator 223 and acoustic transducer 121 may be configured to produce any variety of frequencies, e.g., frequencies below the audible range, in the audible range, and/or above the audible range may be used. In some embodiments, frequencies may comprise at least one frequency in the audible range. The audible range generally comprises frequencies from about 20 Hertz to about 20,000 Hertz.

Echogram generator 223 and microphone 122 may be configured to receive, sample, and/or record acoustic reflections 116 as echogram data 113 in the echogram data store 226. Acoustic reflections 116 received at microphone 122 may be converted into acoustic reflection signals 112 at the microphone 122, and may be sampled and/or recorded by echogram generator 223 as echogram data 113 in the echogram data store 226.

The acoustic reflections 116 generally correspond to the acoustic pulses 115, and may also comprise information about the skin surface 133 as well as subsurface skin layers such as 131 and 132, and features such as 134. Different materials reflect sound differently, and so properties of the skin surface 133, subsurface skin layers 131 and 132, and features 134 may be detectable from echogram data 113 corresponding to the acoustic reflections. The echogram data 113 may be used by echogram processing 224 to analyze the skin as described herein.

Acoustic reflections 116 may comprise a variety of reflected frequencies. In general, higher frequency reflections may carry information about smaller-scale properties of the skin surface 133, subsurface layers 131, 132, and features such as 134, while lower-frequency reflections may carry information about larger-scale properties of the skin surface 133, subsurface layers 131, 132, and features such as 134. Higher frequency reflections have shorter wavelengths, because frequency and wavelength are inversely proportional with respect to one another. Echogram data 113 may comprise a range of characteristics corresponding to a range of different acoustic reflection wavelengths. Echogram data 113 may also comprise subwavelength acoustic reflection characteristics. Subwavelength acoustic reflection characteristics are defined herein as acoustic reflection characteristics corresponding to one or more reflecting features (such as 134) comprising at least one dimension smaller than a corresponding acoustic pulse wavelength from the series of acoustic pulses.

Certain subwavelength acoustic reflection characteristics may correspond to Rayleigh scattering effects in the skin. Rayleigh scattering is scattering by subwavelength features, and therefore provides enhanced sensitivity to echogram detection of subwavelength features. Rayleigh scattering may for example allow for detecting skin hardening and/or other subwavelength features, whether on or under a skin surface, using pulses in or around the audible frequency range. Furthermore, Rayleigh scattering can be relatively insensitive to angle of view, which provides for more robust field measurement of subwavelength features. In some embodiments, a plurality of subwavelength acoustic reflection characteristics may be assembled to create a map of subwavelength features in the skin.

In some embodiments, the echogram generator 223 may be adapted to correlate information regarding the acoustic pulses 115 with information from the acoustic reflections 116 to produce the echogram data 113. For example, acoustic reflections 116 may be correlated to frequency information of the acoustic pulses 115.

Echogram generator 223 may be configured to calibrate processing of echogram data 113 to account for error in producing acoustic pulses 121 and receiving acoustic reflections 122. For example, where echogram generator 223 is configured as part of an application executable by a mobile device, the echogram generator 223 may encounter a variety of acoustic transducers 121 and/or microphones 122 on devices in the field. Some transducers and/or microphones may be not be capable of producing or receiving certain frequencies, or may produce or receive frequencies inaccurately, or may produce certain frequencies in addition to those dictated by the echogram generator 223. Accordingly, the echogram generator 223 may be adapted to produce one or more calibration pulses, and may then measure acoustic reflections to determine the capabilities of the device 200. A calibration pulse may comprise a pulse of one or more predetermined calibration frequencies. The echogram generator 223 may be configured to adapt subsequent acoustic pulses 115 as well as echogram data 113 to account for any error in pulse production and measurement, as determined from the calibration pulse.

In some embodiments, the echogram generator 223 may be configured to determine the distance between the acoustic transducer 121 and/or microphone 122 and the skin surface 133. For example, echogram generator 223 may be configured to calculate distance using a measured amplitude difference between acoustic pulses 115 and corresponding acoustic reflections 116, and an expected pulse attenuation rate. Echogram generator 223 may also be configured to measure time delay between generating a pulse at the transducer 121 and receiving a pulse at the microphone 122, and may calculate distance using the time delay and the speed of sound (roughly 340 meters per second in air, at sea level).

Echogram processing 224 may be configured to use the echogram data 113 in the echogram data store 226 to facilitate diagnosis of a skin condition. A variety of configuration options for the echogram processing 224 are disclosed. In one example, echogram processing 224 may identify one or more characteristics of echogram data 113, and may look up the characteristics in the skin condition library 227 to determine or identify a skin condition 114 corresponding to the echogram data 113. For example, echogram processing 224 may be configured to extract subwavelength acoustic reflection characteristics of the echogram data 113, and compare the subwavelength acoustic reflection characteristics to a set of characteristics in the skin condition library 227 to identify matching characteristics in the skin condition library 227. When a matching characteristic is found, a skin condition 114 corresponding to the matching subwavelength acoustic reflection characteristics in the skin condition library 227 may be identified to the echogram processing 224. In various additional embodiments, other characteristics of the echogram data 113 may also be extracted and used by echogram processing 224 to identify corresponding skin conditions.

Furthermore, echogram processing 224 may be configured to store echogram data 113 and/or extracted characteristics as comparison data 119 in the comparison data store 228, for subsequent use in future skin condition identification operations. Comparison data 119 may also comprise image data 118 and optionally identification information comprising, for example, identifiers for the scanned subject (e.g. person's name), a location of the scanned skin surface (e.g. right shoulder blade), and/or date of the echogram.

In various additional embodiments, echogram processing 224 may furthermore be adapted to identify characteristics of image data 118 and/or comparison data 119, and characteristics of image data 118 and/or comparison data 119 may also be used in looking up skin conditions in the skin condition library 227. Echogram processing 224 may output an identified skin condition 114 to output devices 260, e.g., echogram processing 224 may output an identification of a skin condition 114 to a display.

In some embodiments, echogram processing 224 may be adapted to look up skin conditions in a skin condition library 227 on the network node 291. Echogram characteristics, image characteristics, and characteristics of comparison data 119 may be provided to the network node 291 as skin condition ID data 117. Network node 291 may be configured to compare the skin condition ID data 117 to data stored in the skin condition library 227 as described above. Network node 291 may be configured to return one or more identified skin conditions 114 to the computing device 200.

In some embodiments, echogram processing 224 may be configured to electronically communicate skin condition ID data 117 to a medical service provider network node 292 for further analysis. Dermatologists or other trained professionals may be available for analysis of the skin condition ID data 117. Skin condition ID data 117 may for example be provided to medical service provider network node 292 in the form of an email to a medical service provider. The medical service provider may then analyze the skin condition ID data 117 and communicate any findings with the patient using any appropriate communications channel.

In some embodiments, echogram processing 224 may be configured to secure data stored on the device 200 as well as any data communicated outside the device 200 to protect the privacy of skin health data. For example, echogram processing 224 may be configured to use encryption to protect echogram data store 226, image data store 229, comparison data store 228, and/or any other data stored on the device 200. Data may be encrypted using a password supplied by a user of the device 200. Echogram processing 224 may furthermore be adapted to encrypt any data sent to network nodes 291 and 292.

In some embodiments, the methods, devices, and/or systems related to detecting skin conditions described herein may be combined with any of the technologies described in U.S. patent application Ser. No. 12/714,011, filed Feb. 26, 2010, entitled "MULTIDIRECTIONAL SCAN AND ALGORITHMIC SKIN HEALTH ANALYSIS".

Figure 2:
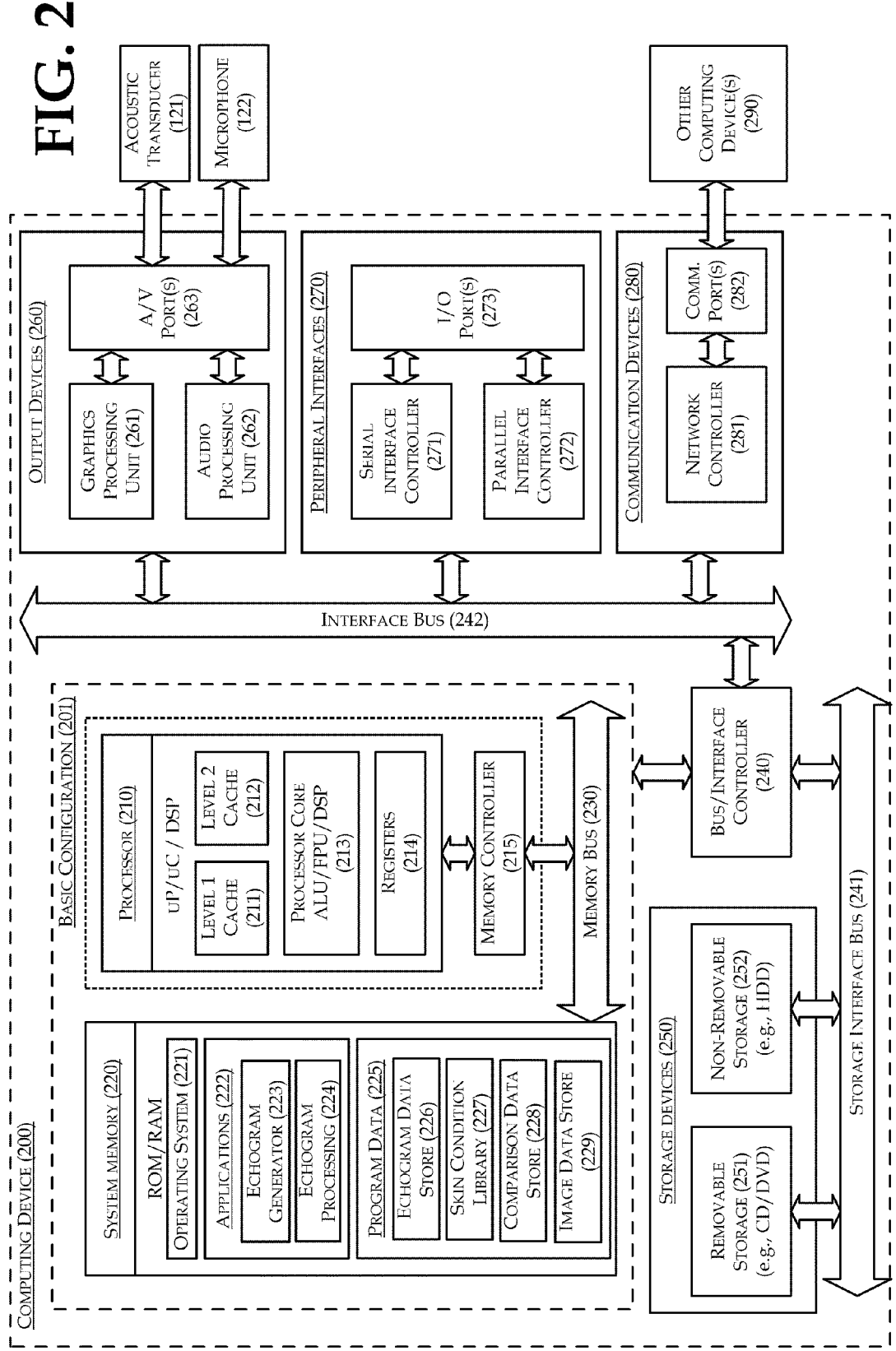
FIG. 2 is a block diagram illustrating a computing device as one example of the device illustrated in FIG. 1.

FIG. 2 is a block diagram of a computing device 200 as one example of the device illustrated in FIG. 1, arranged in accordance with at least some embodiments of the present disclosure. In a very basic configuration 201, computing device 200 may include one or more processors 210 and system memory 220. A memory bus 230 may be used for communicating between the processor 210 and the system memory 220.

Depending on the desired configuration, processor 210 may be of any type including but not limited to a microprocessor (µP), a microcontroller (µC), a digital signal processor (DSP), or any combination thereof. Processor 210 may include one or more levels of caching, such as a level one cache 211 and a level two cache 212, a processor core 213, and registers 214. The processor core 213 may include an arithmetic logic unit (ALU), a floating point unit (FPU), a digital signal processing core (DSP Core), or any combination thereof. A memory controller 215 may also be used with the processor 210, or in some implementations the memory controller 215 may be an internal part of the processor 210.

Depending on the desired configuration, the system memory 220 may be of any type including but not limited to volatile memory (such as RAM), non-volatile memory (such as ROM, flash memory, etc.), or any combination thereof. System memory 220 typically includes an operating system 221, one or more applications 222, and program data 225. Applications 223-224 may include, for example, echogram generator module(s) 223 and echogram processing module(s) 224. Program data 226-227 may include echogram data store 226, skin condition library 227, comparison data store 228, and image data store 229 that may be used by applications 223-224.

Computing device 200 may have additional features or functionality, and additional interfaces to facilitate communications between the basic configuration 201 and any required devices and interfaces. For example, a bus/interface controller 240 may be used to facilitate communications between the basic configuration 201 and one or more data storage devices 250 via a storage interface bus 241. The data storage devices 250 may be removable storage devices 251, non-removable storage devices 252, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives, to name a few. Example computer storage media may include volatile and nonvolatile, removable and non-removable media implemented in any method or technology for storage of information, such as computer readable instructions, data structures, program modules, or other data.

System memory 220, removable storage 251, and non-removable storage 252 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that may be used to store the desired information and that may be accessed by computing device 200. Any such computer storage media may be part of device 200.

Computing device 200 may also include an interface bus 242 for facilitating communication from various interface devices (e.g., output interfaces, peripheral interfaces, and communication interfaces) to the basic configuration 201 via the bus/interface controller 240. Example output devices 260 include a graphics processing unit 261 and an audio processing unit 262, which may be configured to communicate to various external devices such as a display, acoustic transducer 121 and microphone 122 via one or more A/V ports 263. Example peripheral interfaces 270 may include a serial interface controller 271 or a parallel interface controller 272, which may be configured to communicate through either wired or wireless connections with external devices such as input devices (e.g., keyboard, mouse, pen, voice input device, touch input device, etc.) or other peripheral devices (e.g., printer, scanner, etc.) via one or more I/O ports 273. Other conventional I/O devices may be connected as well such as a mouse, keyboard, and so forth. An example communications device 280 includes a network controller 281, which may be arranged to facilitate communications with one or more other computing devices 290 such as may comprise network nodes 291 and 292 illustrated in FIG. 1, over a network communication via one or more communication ports 282.

The computer storage media may be one example of a communication media. Communication media may typically be embodied by computer readable instructions, data structures, program modules, or other data in a modulated data signal, such as a carrier wave or other transport mechanism, and include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR), and other wireless media.

Computing device 200 may be implemented as a portion of a small-form factor portable (or mobile) electronic device such as a cell phone, a personal data assistant (PDA), a personal media player device, a wireless web-watch device, a personal headset device, an application-specific device, or a hybrid device that include any of the above functions. Computing device 200 may also be implemented as a personal computer including both laptop computer and non-laptop computer configurations.

Figure 3:
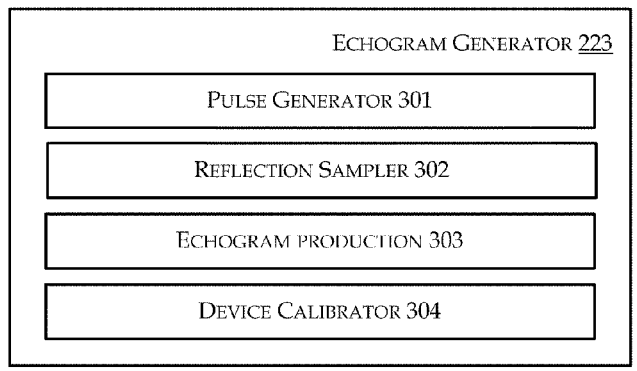
FIG. 3 is a block diagram illustrating example components of an echogram generator module.

FIG. 3 is a block diagram illustrating example components of an echogram generator module, arranged in accordance with at least some embodiments of the present disclosure. Echogram generator module 223 may comprises pulse generator 301, reflection sampler 302, echogram production 303, and device calibration 304.

The pulse generator 301 may be configured to generate acoustic pulses 115, where a series of acoustic pulses may be produced in rapid succession. For example, in some embodiments, a series of around 40 pulses may be produced, each pulse of about 0.01 seconds in length. Each pulse may comprise one or more frequencies that may be directed at a skin surface for the purpose of measuring acoustic reflections 116 from the skin, to produce echogram data 113.

In some embodiments, a pulse may comprise a chirp. A chirp is a signal in which the frequency may increase ('up-chirp') or decrease ('down-chirp') with time. A chirp may for example be linear, exponential, or according to any other desired trajectory as will be appreciated. An acoustic pulse may be a chirp comprising a start frequency and an end frequency that is different from the start frequency. For example, chirp start frequencies may range from about 4 kilo-Hertz (kHz) to about 12 kHz. Chirp end frequencies may be about 500 Hz higher than the start frequency. This disclosure is not limited to these example values.

In some embodiments, a pulse may be generated according to a window function. A window function is a function that is zero-valued outside of some chosen interval. Window functions may produce rectangular windows, Hamming windows, Hann windows, Cosine windows, Gauss windows, and a variety of other window types.

The reflection sampler 302 may be configured to sample and record acoustic reflection signals 112 produced by microphone 122 in response to received acoustic reflections 116. Echogram production 303 may be configured to correlate the acoustic reflection samples produced by the reflection sampler 302 with acoustic pulse data, such as data regarding frequencies of the acoustic pulses 115. Device calibration 304 may be configured to provide calibration frequencies for use by the pulse generator 301, and may subsequently provide device-specific frequency ranges to the pulse generator 301 as well as calibration error data to the echogram production 303, for use in adjusting echogram data.

Figure 4:
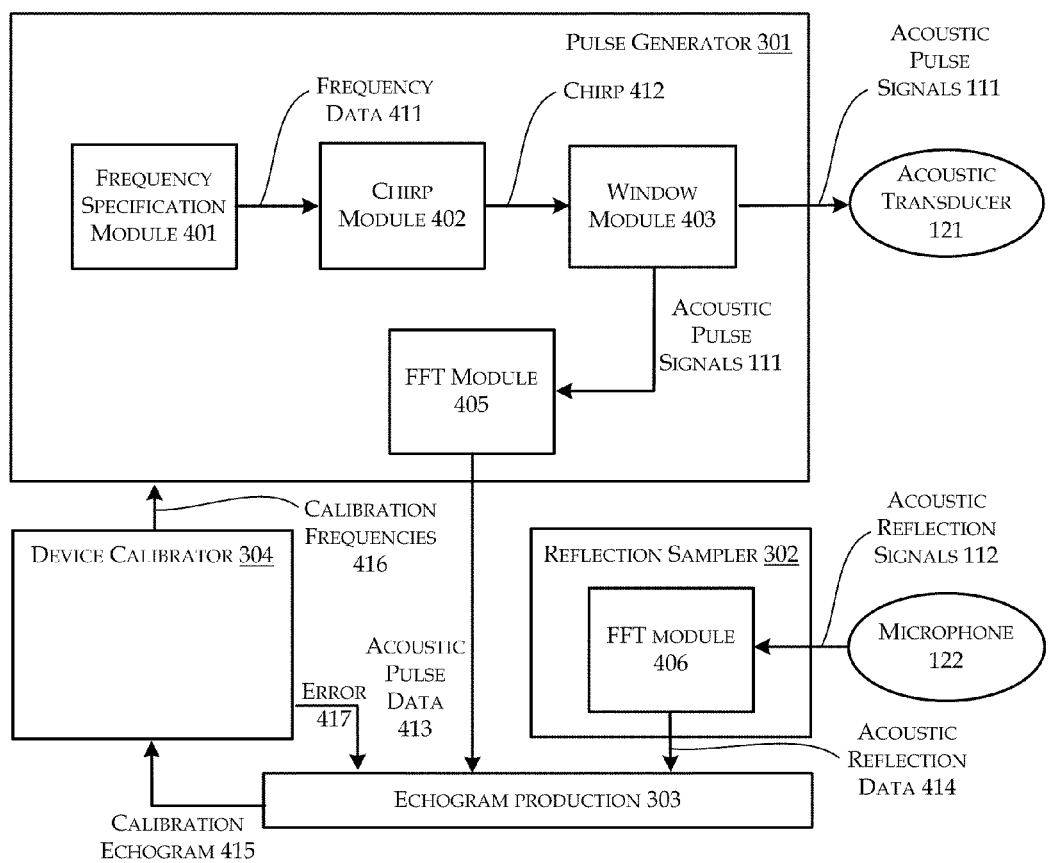
FIG. 4 is a block diagram illustrating example configuration and interaction of the echogram generator components illustrated in FIG. 3.

FIG. 4 is a block diagram illustrating example configuration and interaction of the echogram generator components illustrated in FIG. 3, arranged in accordance with at least some embodiments of the present disclosure. FIG. 4 illustrates the components of FIG. 3, including the pulse generator 301, reflection sampler 302, echogram production 303, and device calibration 304, and FIG. 4 also illustrates an acoustic transducer 121 and a microphone 122. The pulse generator 301 may comprise an adjustable frequency generator 401, a chirp module 402, a window module 403, and a Fast Fourier Transform (FFT) module 405. The reflection sampler 302 may comprise an FFT module 406.

The pulse generator 301 may comprise an adjustable frequency generator 401, a chirp module 402, a window module 403, and a Fast Fourier Transform (FFT) module 405. The frequency generator 401 may be effective to provide frequency data 411 to the chirp module. Frequency data 411 may for example specify one or more chirp start frequencies and/or chirp end frequencies. Chirp module 402 may be effective to produce a chirp signal 412 to the window module 403. The window module 403 may be effective to window the chirp signal according to a window function, and may output a windowed chirp as an acoustic pulse signal 111 to the acoustic transducer. The acoustic pulse signal 111 may also be provided to the FFT module, which may be effective to perform an FFT on the acoustic pulse signal 111 and output acoustic pulse data 413 to the echogram production module 303.

The reflection sampler 302 may comprise an FFT module 406, which is adapted to receive acoustic reflection signals 112 from the microphone 122, and output acoustic reflection data 414 to the echogram production module 303. The echogram production module 303 may be configured to produce echogram data using the acoustic pulse data 413 and the corresponding acoustic reflection data 414.

An arrangement such as FIG. 4 may be calibrated using a device calibrator 304. In some embodiments, the device calibrator 304 may provide calibration frequencies 416 to the pulse generator 301. The pulse generator 301 may be configured to generate acoustic pulses according to the calibration frequencies 416, and the echogram production module 303 may be configured to produce a calibration echogram 415 corresponding to the calibration frequencies. The device calibrator 304 may be configured to use the calibration echogram 415 to determine which frequencies a device is capable of producing, and any error 417 which may be used by the echogram production module 303 to improve accuracy of echogram data produced by a particular device. The available frequencies and the error 417 may be provided to pulse generator 301 and to echogram production module 303, to allow the pulse generator 301 and echogram production module 303 to dynamically reconfigure the outgoing pulses and/or echogram production processing to account for available frequencies and error 417.

Figure 5:
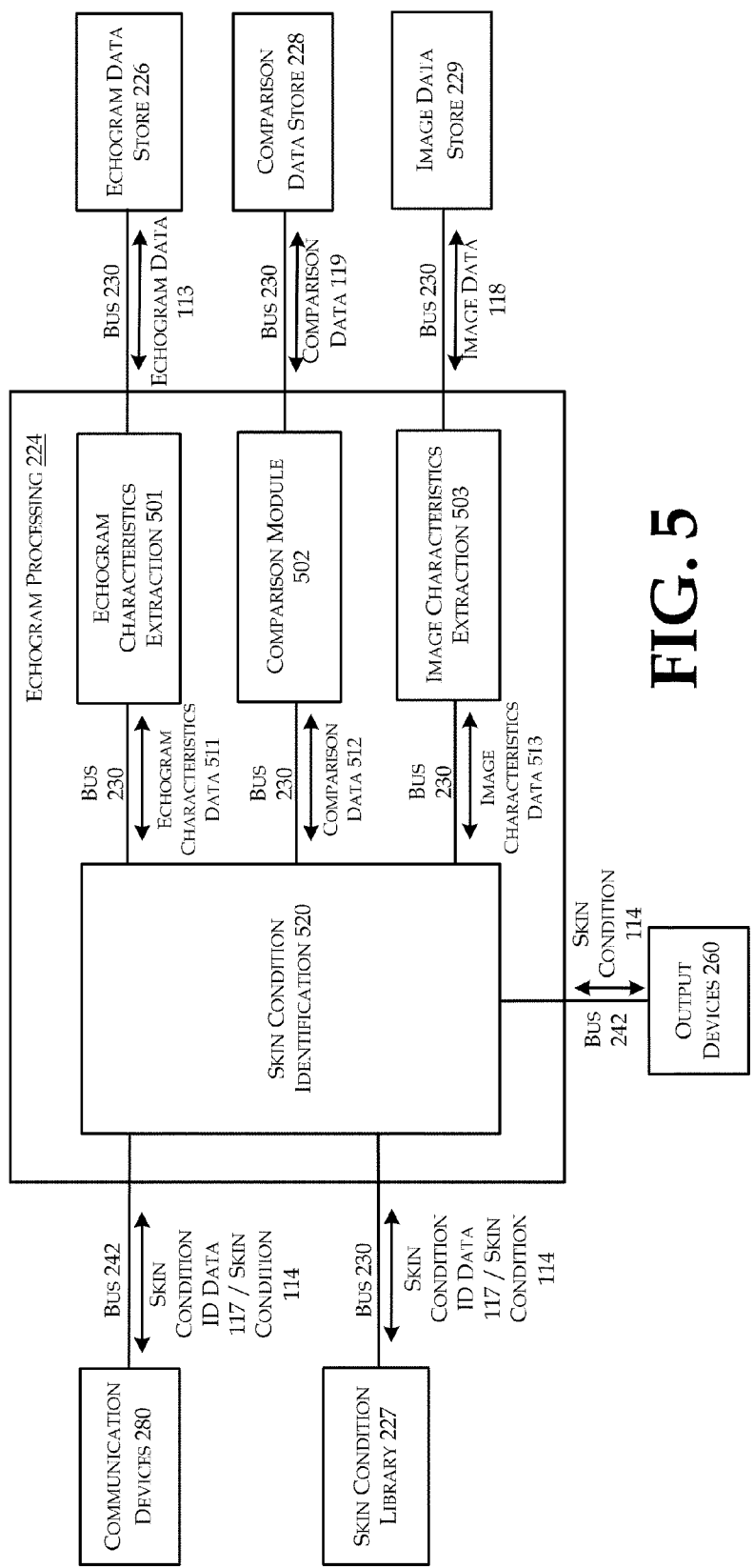
FIG. 5 is a is a block diagram illustrating example components of an echogram processing module and interactions thereof.

FIG. 5 is a is a block diagram illustrating example components of an echogram processing module and interactions thereof, arranged in accordance with at least some embodiments of the present disclosure. Echogram processing module 224 may comprise one or more of an echogram characteristics extraction module 501, a comparison module 502, an image characteristics extraction module 503, and/or a skin condition identification module 520. Echogram processing module 224 may be adapted to interact with one or more of an echogram data store 226, a comparison data store 228 and/or an image data store 229. Echogram processing module 224 may also be adapted to interact with one or more of communication devices 280, a skin condition library 227, and/or output devices 260.

Echogram characteristics extraction module 501 may be adapted to communicate echogram data 113 with echogram data store 226 via bus 230. Echogram characteristics extraction module 501 may also be adapted to communicate echogram characteristics data 511 with skin condition identification module 520 via bus 230. Comparison module 502 may be adapted to communicate comparison data 119 with comparison data store 228 via bus 230. Comparison module 502 may also be adapted to communicate comparison data 512 with skin condition identification module 520 via bus 230. Image characteristics extraction module 503 may be adapted to communicate image data 118 with image data store 229 via bus 230. Image characteristics extraction module 503 may also be adapted to communicate image characteristics data 513 with skin condition identification module 520 via bus 230.

Furthermore, skin condition identification module 520 may be adapted to communicate skin condition ID data 117 and skin condition 114 with communication devices 280 via bus 242. Skin condition identification module 520 may also be adapted to communicate skin condition ID data 117 and skin condition 114 with skin condition library 227 via bus 230. Skin condition identification module 520 may also be adapted to communicate skin condition 114 with output devices 260 via bus 242.

Echogram processing module 224 may be configured to facilitate identification of one or more skin conditions using echogram data, along with a variety of other data which may be useful in identifying the various skin conditions. In some embodiments, echogram processing module 224 may display echogram data 113 at output devices 260 and/or forward echogram data 113 via communication devices 280 to a medical service provider for analysis. Echogram processing module 224 may be configured to provide UI to allow a user to correlate image data 118 showing an image of the skin, and/or comparison data 119 showing previous echograms of the skin, for analysis in conjunction with the echogram data 113.

Echogram processing module 224 may also be configured to provide electronic diagnosis functions, for example by extracting characteristics from the various applicable data and comparing the extracted characteristics to a skin condition library 227 to identify a skin condition 114. In some embodiments, echogram characteristics extraction module 501 may be configured to extract echogram characteristics data 511 from echogram data 113. Echogram characteristics data 511 may for example comprise reflection signatures at one or more pulse frequencies and/or subwavelength characteristics. A variety of echogram characteristics may over time become associated with identifiable skin conditions, and this disclosure is not limited to any particular characteristics. In some embodiments, subwavelength characteristics may be extracted as these characteristics may be advantageous in identifying certain skin properties.

Comparison module 502 and image characteristics extraction 503 may be configured to extract comparison data 512 and image characteristics data 513, and provide these data to the skin condition identification module 520. Again, the extracted characteristics may be any data values and/or patterns relevant to identifying a skin condition.

Skin condition identification module 520 may be configured to acquire any echogram characteristics data 511, comparison characteristics data 512 and image characteristics data 513, and to use some or all of data 511, 512, and 513 as skin condition ID data 117, to facilitate determination of a skin condition 114 by passing the skin condition ID data 117 to the communication devices 280 and/or looking up a skin condition 114 corresponding to the skin condition ID data 117 in the skin condition library 227.

In some embodiments, the skin condition library 227 may not contain an exact match of the skin condition ID data. The skin condition identification module 520 may be configured to perform "fuzzy" or approximate matching techniques to determine potentially applicable skin conditions. One example approach for approximate matching may comprise measuring a number of primitive operations necessary to convert data sets to identical data.

The skin condition library 227 may comprise a plurality skin conditions corresponding to echogram characteristics 511 and/or comparison and image characteristics 511 and 512. For example, the skin condition library 227 may comprise a plurality melanoma type skin conditions as well as malignant nevi conditions, and cosmetic conditions such as scars, acne, moles and/or freckles. The skin condition processing module(s) 224 may be configured to retrieve any skin condition 114 corresponding echogram characteristics in the library 227 that match the echogram characteristics 511 from echogram data 113.

In some embodiments, a skin condition 114 may be identified in any of a variety of forms. For example, in some embodiments a skin condition 114 may comprise a medical risk associated with a skin condition 114. If an echogram characteristic 511 is identified as an X % melanoma risk (where X is 0%-100%) the melanoma (or other condition) probability may be retrieved. Similarly, where a benign cosmetic blemish is identified, data identifying a skin condition as a cosmetic blemish and optionally suggesting or providing cosmetic removal options may be provided.

In some embodiments, echogram processing 224 may be configured to facilitate identification of skin conditions using alternate techniques. For example, instead of extracting echogram characteristics and comparing the extracted characteristics to characteristics in a skin condition library 227, an echogram may be scanned for characteristics identified in a skin condition library 227 as corresponding to certain known skin conditions.

Figure 6:
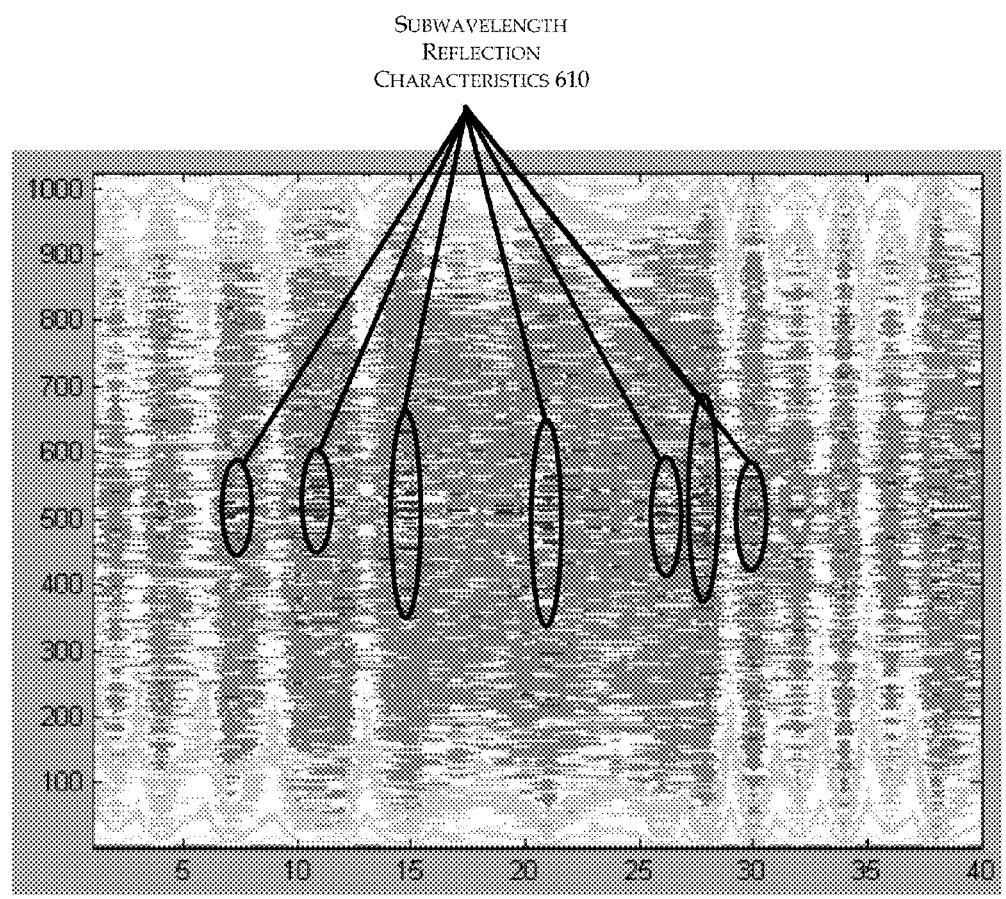
FIG. 6 is an example echogram comprising subwavelength reflection characteristics.

FIG. 6 is an example echogram comprising subwavelength reflection characteristics, arranged in accordance with at least some embodiments of the present disclosure. FIG. 6 provides a visual representation of echogram data 113 corresponding to an echogram of a chest. In FIG. 6, chirp start frequency is represented along the X-axis and sample number is represented along the Y-axis, each sample being a slightly different frequency in the illustrated embodiment, due to the characteristics of the chirp. As may be appreciated, the echogram provides a variety of characteristics which may indicate any of a wide variety of information about the reflecting surface. Example subwavelength reflection characteristics 610 are indicated.

Figure 7:
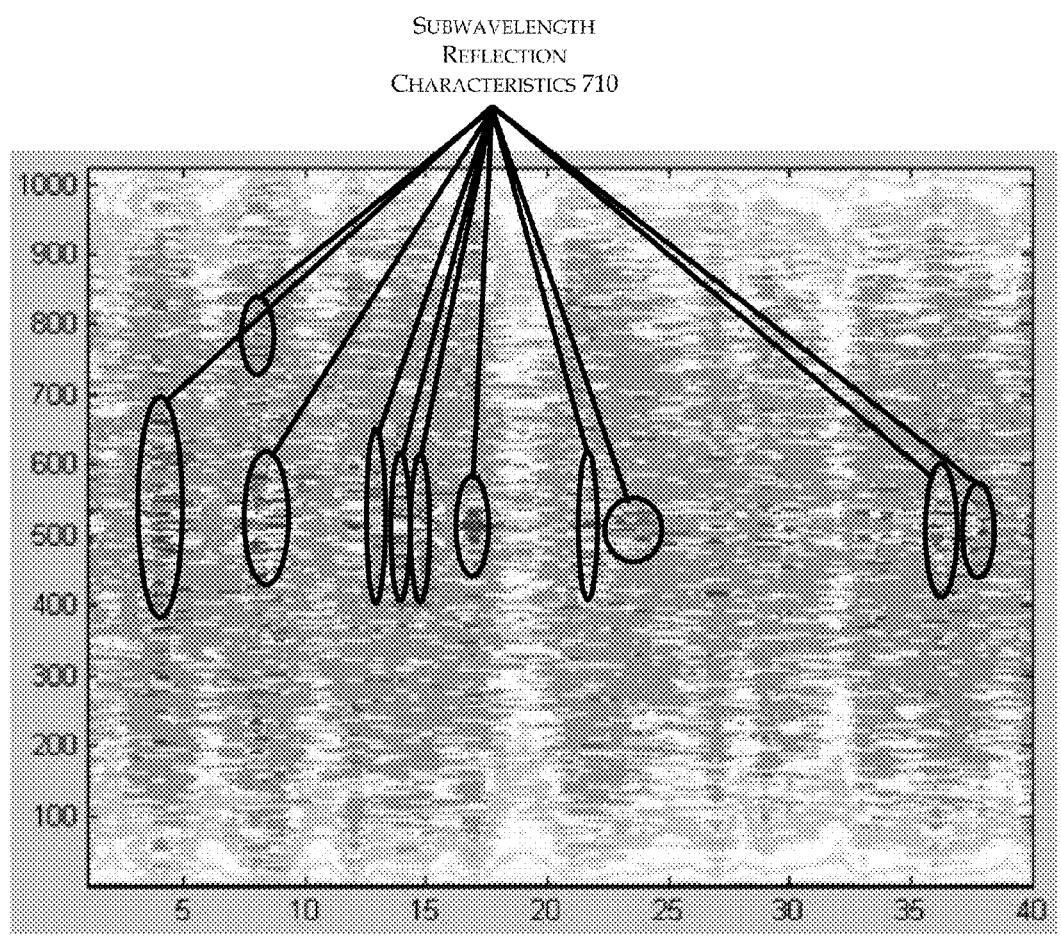
FIG. 7 is an example echogram comprising subwavelength reflection characteristics.

FIG. 7 is an example echogram comprising subwavelength reflection characteristics, arranged in accordance with at least some embodiments of the present disclosure. FIG. 7 provides a visual representation of echogram data 113 corresponding to an echogram of a dog. In FIG. 7, chirp start frequency is represented along the X-axis and sample number is represented along the Y-axis. Again, each sample is a slightly different frequency in the illustrated embodiment, due to the characteristics of the chirp. As may be appreciated, the echogram provides a variety of characteristics which may indicate any of a wide variety of information about the reflecting surface and/or subsurface features. Example subwavelength reflection characteristics 710 are indicated. Comparing the echogram of FIG. 7 to the echogram of FIG. 6, it is readily apparent that any of a variety of characteristics may be used to differentiate the skin of a human chest from the skin of a dog comprising the condition of being covered with dog fur. A result similar to FIG. 7 may be obtainable for example with a hairy human skin sample. Further characteristics of the echograms may be used to further identify characteristics of the skins from the echogram data.

Figure 8:
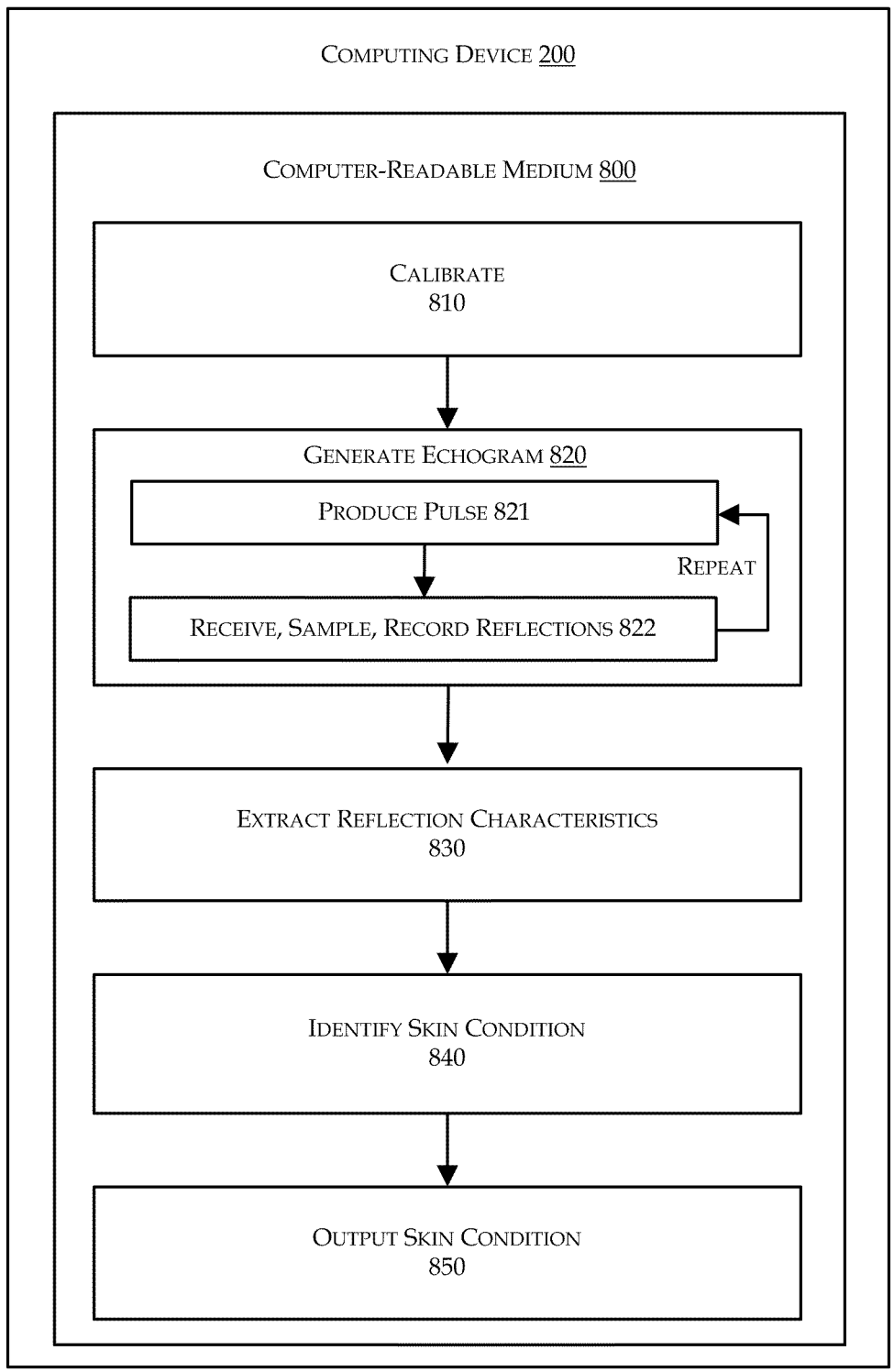
FIG. 8 is flow diagram illustrating an example method configured to generate echogram data and analyze the echogram data to determine potential skin conditions; all arranged in accordance with at least some embodiments of the present disclosure.

FIG. 8 is flow diagram illustrating an example method configured to generate echogram data and analyze the echogram data to determine potential skin conditions, arranged in accordance with at least some embodiments of the present disclosure. The example flow diagram may include one or more operations/modules, functions or actions as illustrated by blocks 810, 820 (comprising blocks 821 and 822), 830, 840, and 850, which represent operations as may be performed in a method, functional modules in a computing device 200, and/or instructions as may be recorded on a computer readable medium 800. The illustrated blocks 810, 820, 821, 822, 830, 840, and 850 may be arranged to provide functional operations including one or more of "Calibrate" at block 810, "Generate Echogram" at block 820, "Produce Pulse" at block 821, "Receive, Sample, and Record Reflections" at block 822, "Extract Reflection Characteristics" at block 830, "Identify Skin Condition" at block 840, and/or "Output Skin Condition" at block 850.

In FIG. 8, blocks 810, 820, 821, 822, 830, 840, and 850 are illustrated as being performed sequentially, with block 810 first and block 850 last, with a repetitive loop comprising blocks 821 and 822. It will be appreciated however that these blocks may be re-ordered as convenient to suit particular embodiments, and that these blocks or portions thereof may be performed concurrently in some embodiments. It will also be appreciated that in some examples various blocks may be eliminated, divided into additional blocks, and/or combined with other blocks.

In block 810, "Calibrate", computing device 200 may be configured to produce one or more calibration pulses to calibrate a device for detecting the skin condition. In some embodiments, a calibration pulse may comprise a multi-frequency chirp configured to test the frequencies that may be used for subsequently generating an echogram. Acoustic reflections corresponding to the calibration pulse(s) may be received via a microphone and a calibration echogram may be produced. The calibration echogram may be analyzed to determine frequencies in the calibration pulse that were successfully produced and received, frequencies in the calibration pulse that were not successfully reproduced and received, and/or any error in producing and receiving calibration pulse frequencies.

For example, if a calibration pulse includes a 15 kHz frequency, and the 15 kHz frequency appears in the echogram as expected, then the 15 kHz frequency may be determined to be a frequency that may be successfully produced and received. If a calibration pulse includes a 15 kHz frequency, and the 15 kHz frequency does not appear in the echogram as expected, then the 15 kHz frequency may be determined to be a frequency that cannot be successfully produced and received. In response to a determination that a frequency (such as 15 kHz) does not appear as expected, in some embodiments a device calibrator 304 may be configured to test whether compensation is possible, for example by modifying the unavailable frequency. For example, a device calibrator 304 may be configured to increase the 15 kHz component and try again to produce the reflection. If a calibration pulse includes frequencies from 15 kHz to 30 kHz, but the echogram instead shows frequencies from about 15.5 kHz to about 30.5 kHz, then it may be determined from the echogram data that there is a 0.5 kHz error in producing the and receiving calibration pulse frequencies.

Block 810 may be configured to adjust echogram generation based on information determined using the calibration pulse. For example, in some embodiments the acoustic pulse frequencies may be adjusted to account for any error, or to avoid frequencies that are unavailable. In some embodiments, data corresponding to sampled acoustic reflections may be adjusted to improve accuracy based on information gathered in block 810. Block 810 may be followed by block 820.

In block 820, "Generate Echogram", echogram data may be generated for example using an echogram generator 223, acoustic transducer 121, and microphone 122 as discussed herein. Block 820 may comprise a "Produce Pulse" block 821, which may be configured to produce (e.g., transmit) a series of acoustic pulses, and a "Receive, Sample, and Record Reflections" block 822, which may be configured to receive acoustic reflections corresponding to the acoustic pulses, sample received acoustic reflections, and record samples as echogram data. In some embodiments, blocks 821 and 822 may be configured in a repeating loop, as shown, whereby a pulse may be transmitted, followed by receiving, sampling, and recording the reflections that result from the transmitted pulse, followed by another pulse and so on until processing of acoustic pulses of all desired frequencies is completed. The series of acoustic pulses may be directed at a skin surface. In some embodiments, the series may comprise a plurality of frequencies and at least one frequency in the audible range. Block 820 may be followed by block 830.

In block 830, "Extract Reflection Characteristics", reflection characteristics of the echogram may be extracted, for example by an echogram processing module 224 as discussed herein, for use in identifying a skin condition. In some embodiments, subwavelength acoustic reflection characteristics may be extracted, wherein the subwavelength acoustic reflection characteristics correspond to one or more reflecting features comprising at least one dimension smaller than a corresponding acoustic pulse wavelength from the series of acoustic pulses. However, any reflection characteristics may be identified as useful in identifying skin conditions, and this disclosure is not limited to any characteristics in particular.

In some embodiments, characteristics may also be extracted from image data corresponding to the skin involved in the echogram, as may comparison characteristics from previous echograms of the skin. Image data characteristics and comparison characteristics may be used along with reflection characteristics in block 840. Furthermore, extracted reflection characteristics may be stored as comparison data for future skin condition identification procedures. Block 830 may be followed by block 840.

In block 840, "Identify Skin Condition", a skin condition corresponding to reflection characteristics extracted in block 830 may be identified, for example by an echogram processing module 224 as discussed herein. In some embodiments, block 840 may comprise electronically identifying a skin condition by comparing extracted subwavelength acoustic reflection characteristics to a skin condition library that correlates subwavelength acoustic reflection characteristics with skin conditions.

In some embodiments, block 840 may comprise electronically sending skin condition ID data 117 to a medical provider for further analysis. Therefore, a positive identification of a skin condition need not be completed in all embodiments of block 840. Some embodiments may comprise initiating or otherwise facilitating identification, which may be completed at a later time and optionally by a dermatologist or other skin care professional. Block 840 may be followed by block 850.

In block 850, "Output Skin Condition", an identification of a skin condition may be output to an output device. For example, an identification of a skin condition may be output by an echogram processing module 224 to a display. In some embodiments, block 850 may be omitted, for example where block 840 comprises initiating skin condition identification by sending echogram data to a medical service provider, rather than electronically identifying a skin condition at the device. In some embodiments, the skin condition may comprise a risk of certain skin conditions, and optionally additional information such as treatment options and contact information for dermatologists or other professionals available to consult regarding the skin condition.

There is little distinction left between hardware and software implementations of aspects of systems; the use of hardware or software is generally (but not always, in that in certain contexts the choice between hardware and software may become significant) a design choice representing cost vs. efficiency tradeoffs. There are various vehicles by which processes and/or systems and/or other technologies described herein may be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/ or quantities). A typical data processing system may be implemented utilizing any suitable commercially available components, such as those typically found in data computing/ communication and/or network computing/communication systems. The herein described subject matter sometimes illustrates different components contained within, or connected with, different other components. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While certain example techniques have been described and shown herein using various methods, devices and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

The invention claimed is:

1. A method for detecting one or more skin conditions associated with a skin of a subject, the method comprising:
   generating echogram data, comprising:
      transmitting a series of acoustic pulses, wherein the series of acoustic pulses are directed at a surface of the skin, and wherein the series of acoustic pulses comprises a plurality of frequencies with at least one frequency being in the audible range;
      receiving acoustic reflections corresponding to the acoustic pulses;
      sampling the received acoustic reflections to generate samples; and
      recording the samples as echogram data;
   extracting by using a processor a subwavelength acoustic reflection characteristic of the echogram data, wherein the subwavelength acoustic reflection characteristic corresponds to a reflecting feature comprising at least one dimension smaller than a corresponding acoustic pulse wavelength from the series of acoustic pulses; and
   identifying the one or more skin conditions that correspond to the extracted subwavelength acoustic reflection characteristic.

2. The method of claim 1, wherein identifying the one or more skin conditions comprises comparing the extracted subwavelength acoustic reflection characteristic to a library of subwavelength acoustic reflection characteristics and corresponding skin conditions.

3. The method of claim 2, wherein comparing the extracted subwavelength acoustic reflection characteristic to the library of subwavelength acoustic reflection characteristics comprises sending the extracted subwavelength acoustic reflection characteristic to a network node configured to perform the comparing.

4. The method of claim 2, wherein the library of subwavelength acoustic reflection characteristics and corresponding skin conditions comprise one or more subwavelength acoustic reflection characteristics associated with melanoma skin conditions.

5. The method of claim 1, wherein each of the series of acoustic pulses is a Hanning windowed chirp comprising a start frequency and an end frequency different from the start frequency.

6. The method of claim 1, further comprising electronically communicating the echogram data to a medical service provider for further analysis.

7. The method of claim 1, wherein extracting subwavelength acoustic reflection characteristics of the echogram data comprises extracting characteristics corresponding to Rayleigh scattering in the skin.

8. The method of claim 1, further comprising producing a calibration pulse to calibrate a device for detecting the one or more skin conditions.

9. A mobile device configured to detect one or more skin conditions associated with a skin of a subject, the mobile device comprising:
   an acoustic transducer;
   a microphone; and
   a processor arranged in cooperation with the transducer and microphone, wherein the processor is configured to:
      transmit a series of acoustic pulses with the transducer, wherein the series of acoustic pulses are directable at a surface of the skin, and wherein the series comprises a plurality of frequencies with at least one frequency in the audible range;
      sample acoustic reflections received with the microphone;
      record the sampled acoustic reflections as echogram data;
      extract one or more subwavelength acoustic reflection characteristics of the echogram data; and
      identify a skin condition corresponding to one or more of the extracted subwavelength acoustic reflection characteristics, wherein the subwavelength acoustic reflection characteristics correspond to a reflecting feature comprising at least one dimension smaller than a corresponding acoustic pulse wavelength from the series of acoustic pulses.

10. The mobile device of claim 9, wherein the processor is configured to compare the extracted subwavelength acoustic reflection characteristic to a library of subwavelength acoustic reflection characteristics and corresponding the one or more skin conditions to identify the skin condition.

11. The mobile device of claim 10, wherein the processor is configured to send the extracted subwavelength acoustic reflection characteristic to a network node configured to perform the comparison.

12. The mobile device of claim 10, the library of subwavelength acoustic reflection characteristics and corresponding skin conditions comprises one or more subwavelength acoustic reflection characteristics corresponding to one or more melanoma skin conditions.

13. The mobile device of claim 9, wherein the series of acoustic pulses comprises Hanning windowed chirps, each chirp comprising a start frequency and an end frequency different from the start frequency.

14. The mobile device of claim 9, wherein the processor is further configured to electronically communicate the echogram data to a medical service provider for further analysis.

15. The mobile device of claim 9, wherein the processor is configured to extract characteristics corresponding to Rayleigh scattering in the skin.

16. The mobile device of claim 9, wherein the processor is further configured to produce a calibration pulse with the transducer and measure acoustic reflections received at the microphone to calibrate the mobile device for detecting the one or more skin conditions.

17. The mobile device of claim 9, wherein the acoustic transducer and microphone are integrated in the mobile device and are configured for voice communications.

18. A non-transitory computer readable medium having computer executable instructions, executable by a mobile device to detect one or more skin conditions associated with a skin of a subject, the instructions for the mobile device comprising:
   instructions to transmit a series of acoustic pulses, wherein the series of acoustic pulses are directable at a surface of the skin, and wherein the series comprises a plurality of frequencies and at least one frequency in the audible range;
   instructions to sample received acoustic reflections associated with the series of acoustic pulses;
   instructions to record samples of the received acoustic reflections as echogram data; instructions to extract a subwavelength acoustic reflection characteristic of the echogram data, wherein the subwavelength acoustic reflection characteristic corresponds to a reflecting feature comprising at least one dimension smaller than a corresponding acoustic pulse wavelength from the series of acoustic pulses; and instructions to identify the one or more skin conditions corresponding to an extracted subwavelength acoustic reflection characteristic.

19. The computer readable medium of claim 18, wherein the instructions to identify the one or more skin conditions comprise instructions to compare the extracted subwavelength acoustic reflection characteristic to a library of subwavelength acoustic reflection characteristics and corresponding skin conditions.

20. The computer readable medium of claim 19, wherein the instructions to compare the extracted subwavelength acoustic reflection characteristic to a library of subwavelength acoustic reflection characteristics and corresponding skin conditions comprise instructions to send the extracted subwavelength acoustic reflection characteristic to a network node configured to perform the comparison.

21. The computer readable medium of claim 19, wherein the library of subwavelength acoustic reflection characteristics and corresponding skin conditions comprises one or more subwavelength acoustic reflection characteristics corresponding to one or more melanoma skin conditions.

22. The computer readable medium of claim 18, wherein the series of acoustic pulses comprises Hanning windowed chirps, each chirp comprising a start frequency and an end frequency different from the start frequency.

23. The computer readable medium of claim 18, further comprising instructions to electronically communicate the echogram data to a medical service provider for further analysis.

24. The computer readable medium of claim 18, wherein the instructions extracting subwavelength acoustic reflection characteristics of the echogram data comprise instructions to extract characteristics corresponding to Rayleigh scattering in the skin.

25. The computer readable medium of claim 18, further comprising instructions to produce a calibration pulse to calibrate the mobile device for detecting the one or more skin conditions.

* * * * *

UNITED STATES PATENT AND TRADEMARK OFFICE
CERTIFICATE OF CORRECTION

| | |
|---|---|
| PATENT NO. | : 8,591,413 B2 |
| APPLICATION NO. | : 12/714060 |
| DATED | : November 26, 2013 |
| INVENTOR(S) | : Kruglick |

Page 1 of 1

It is certified that error appears in the above-identified patent and that said Letters Patent is hereby corrected as shown below:

On the Title Page, in Item (56), under "OTHER PUBLICATIONS", in Column 2, Line 5, delete "asseessment" and insert -- assessment --, therefor.

On Title Page 2, in Item (56), under "OTHER PUBLICATIONS", in Column 2, Lines 7-8, delete "newtechnologies for the in vivodiagnosis" and insert -- new technologies for the in vivo diagnosis --, therefor.

In the Specification

In Column 2, Line 4, delete "is a is a" and insert -- is a --, therefor.

In Column 2, Line 11, delete "is flow" and insert -- is a flow --, therefor.

In Column 5, Line 30, delete "pulses 121" and insert -- pulses 115 --, therefor.

In Column 5, Lines 30-31, delete "reflections 122." and insert -- reflections 116. --, therefor.

In Column 10, Line 6, delete "is a is a" and insert -- is a --, therefor.

In Column 12, Line 26, delete "is flow" and insert -- is a flow --, therefor.

Signed and Sealed this
Fifteenth Day of April, 2014

Michelle K. Lee
*Deputy Director of the United States Patent and Trademark Office*